United States Patent [19]

Okada et al.

[11] Patent Number: 5,215,714
[45] Date of Patent: Jun. 1, 1993

[54] IMMUNOAGGLUTINATION MEASUREMENT APPARATUS

[75] Inventors: Satoru Okada; Yoshiteru Mizuno; Takayoshi Izumi; Toshihiro Otani, all of Hyogo, Japan

[73] Assignee: Toa Medical Electronics Co., Ltd., Kobe, Japan

[21] Appl. No.: 709,062

[22] Filed: May 30, 1991

Related U.S. Application Data

[63] Continuation of Ser. No. 272,486, Nov. 16, 1988, abandoned.

[30] Foreign Application Priority Data

Apr. 8, 1988 [JP] Japan .................. 63-86916

[51] Int. Cl.$^5$ ................ G01N 31/02; G01N 35/02
[52] U.S. Cl. .................... 422/64; 422/72; 422/73
[58] Field of Search .................. 422/63-67, 422/72, 73; 436/49

[56] References Cited

U.S. PATENT DOCUMENTS

| | | | |
|---|---|---|---|
| 3,607,099 | 9/1971 | Scordata | 422/73 |
| 3,617,222 | 11/1971 | Matte | 422/73 |
| 3,917,455 | 11/1975 | Bak et al. | |
| 4,130,395 | 12/1978 | Chryssanthou | 422/73 |
| 4,774,055 | 9/1988 | Wakatake et al. | 422/64 |
| 4,818,492 | 4/1989 | Shimizu | 422/63 |
| 4,820,497 | 4/1989 | Howell | 436/49 |
| 4,861,554 | 8/1989 | Sakuma | 422/65 |
| 4,865,810 | 9/1989 | Simon | 422/72 |
| 4,871,683 | 10/1989 | Harris et al. | 422/64 |

FOREIGN PATENT DOCUMENTS 0216026 1/1987 European Pat. Off. .
0282601 9/1988 European Pat. Off. .
PCT/JP/006-
 79 9/1987 PCT Int'l Appl. .

Primary Examiner—Jill A. Johnston
Attorney, Agent, or Firm—Fitch, Even, Tabin & Flannery

[57] ABSTRACT

A buffer solution is sampled from a buffer solution vessel and is dispensed into a reaction vessel on a reaction table by first sampling/dispensing means, and a specimen containing an antigen or antibody to be measured is sampled from a specimen vessel and is dispensed into the reaction vessel by second sampling/dispensing means. A reagent containing insoluble carriers to which is bonded an antibody or antigen that specifically reacts with the antigen or antibody in the specimen is sampled from a reagent vessel and dispensed into the reaction vessel by third sampling/dispensing means. The entire reaction table is shaken continuously during mixing of the buffer solution, reagent and specimen, and the reaction vessel is maintained in an isothermal state. A stable antigen-antibody reaction in the resulting reaction solution is thus promoted to form an agglutinate of the insoluble carriers. The reaction solution is sampled from the reaction vessel and dispensed into a sample chamber by fourth sampling/dispensing means. The dispensed reaction solution is transferred to a detector through which the insoluble carriers are passed and in which a signal is generated based upon a difference in terms of electrical or optical characteristics. The degree of agglutination of the insoluble carriers is obtained as a numerical value, thus making it possible to quantify the antigen or antibody of interest contained in the specimen.

3 Claims, 11 Drawing Sheets

Ⓐ AIR SUPPLY SOURCE
Ⓒ CLEANING FLUID SUPPLY SOURCE
Ⓓ DILUTING SOLUTION SUPPLY SOURCE
Ⓔ WASTE RECOVERY SECTION
Ⓢ SHEACH SOLUTION SUPPLY SOURCE

IMMUNOAGGLUTINATION MEASUREMENT APPARATUS

This application is a continuation of application Ser. No. 272,486 filed Nov. 16, 1988 and now abandoned.

BACKGROUND OF THE INVENTION

This invention relates to an immunoagglutination measurement apparatus for quantifying antigens or antibodies by individually counting the particles of an agglutinate of an insoluble carrier produced by an antigen-antibody reaction.

Measurement of a tumor marker such as alpha-fetprotein (AFP) or carcinoembryonic antigen (CEA) has become extremely important in diagnosing cancers and in observing the progress of cancers.

Radioimmuno assay (RIA) and enzymeimmuno assay (EIA) methods are used in apparatus which measure immunity utilizing the antigen-antibody reaction. As is well known in the art, both methods enable highly sensitive measurement, but the RIA method requires troublesome waste treatment since radioactive substances are used, while the EIA method requires an extended period of time for measurements.

In order to solve these problems, an apparatus has been conceived in which antigen or antibody quantification is carried out by measuring, by a particle counting method, the degree of agglutination that accompanies a latex agglutination reaction utilizing the antigen-antibody reaction. An example is an immunoagglutination measurement apparatus available under the brandname PAMIA-10.

In accordance with this apparatus, a specimen containing an antigen or antibody to be measured is mixed with a reagent containing latex particles to which an antibody or an antigen is bonded that reacts specifically with the antigen or antibody in the specimen. As a result of mixing the specimen and the reagent, an antigen-antibody reaction takes place that causes the latex particles to coalesce together through the medium of the antigen or antibody in the specimen, thereby forming an agglutinate. The latex agglutinate is introduced into a flowcell where it is irradiated with light, the light scattered from the individual particles of the agglutinate is measured, the degree of agglutination is calculated from the number of non-agglutinated particles and the number of agglutinated particles distinguished from each other by measurement of the scattered light, and the degree of agglutination is converted into a figure representing the concentration of antigen or antibody in the specimen. In this way the antigen or antibody of interest within the specimen is quantified.

This conventional immunoagglutination measurement apparatus is in need of certain improvements.

(a) Owing to the sharp increase in the tumor markers to be examined, there is an increase in the amount of specimen and reagent required. A reduction in this amount is desired.

(b) Doubling of processing capability per unit time is strongly desired.

(c) An improvement in operability is required, namely efficient, accurate and safe operation in a small amount of space.

(d) Since mixing for the purpose of stabilizing and promoting the agglutination reaction is performed by rotating a rotor within a reaction vessel, the rotor sustains long-term wear and becomes unbalanced as a result. Thus there the risk of a decline in the mixing efficiency of the rotor.

SUMMARY OF THE INVENTION

Accordingly, an object of the present invention is to provide an immunoagglutination measurement apparatus improved with regard to items (a) through (d) mentioned above.

In accordance with the present invention, the foregoing object is attained by providing an immunoagglutination measurement apparatus for mixing together a specimen, which contains an antigen or antibody to be measured, and a reagent containing insoluble carriers to which is bonded an antibody or antigen that specifically reacts with the antigen or antibody in the specimen, whereby an antigen-antibody reaction takes place that causes the insoluble carriers to mutually agglutinate through the medium of the antigen or antibody in the specimen, introducing the agglutinate to a detecting section whereby a signal based on electrical differences or optical differences among particles is generated, and measuring this signal by particle counting means to obtain the degree of agglutination of the insoluble carriers as a numerical value followed by converting the numerical value, thereby measuring the amount of antigen or antibody contained in the specimen, the apparatus comprising a reversibly rotatable buffer solution table on which a plurality of buffer solution vessels are mounted while maintained in an isothermal state, a reversibly rotatable reagent table on which a plurality of reagent vessels are mounted while maintained in an isothermal state, a reversibly rotatable and shakable reaction table on which a plurality of reaction vessels are supported while maintained in an isothermal state, a transfer section for transferring racks on which specimen vessels are mounted, a dispatch section connected to the transfer section for supplying the racks to the transfer section, a recovery section connected to the transfer section for recovering the racks from the transfer section, first sampling and dispensing means for sampling a buffer solution from the buffer solution vessels on the buffer solution table and dispensing the buffer solution into the reaction vessels on the reaction table, second sampling and dispensing means for sampling a specimen from the specimen vessels and dispensing the specimen into the reaction vessels on the reaction table, third sampling and dispensing means for sampling a reagent from the reagent vessels on the reagent table and dispensing the reagent into the reaction vessels on the reaction table, fourth sampling and dispensing means for sampling a reaction solution, in which an agglutination reaction of the insoluble carriers is brought about by mixing of the buffer solution, specimen and reagent, from the reaction vessels on the reaction table, and dispensing the reaction solution to a sample chamber communicating with a detecting section, and cleansing means for discharging the reaction solution from the reaction vessels and cleansing the reaction vessels.

In operation, a specimen vessel is transferred to a predetermined position by the rack transfer section, a buffer solution is sampled from a predetermined buffer solution vessel and is dispensed into a reaction vessel by the first sampling and dispensing means, and the specimen is sampled from the specimen vessel and dispensed into the reaction vessel by the second sampling and dispensing means. A reagent is sampled from a predetermined reagent vessel and dispensed into the reaction vessel by the third sampling and dispensing means. In successive dispensing and mixing together of the buffer solution, specimen and reagent within the reaction vessel, the entire reaction table is shaken continuously. Since the reaction vessel is maintained in an isothermal state and is shaken and agitated uniformly at such time, the reaction solution, namely the mixture of the buffer solution, specimen and reagent, is stabilized within the reaction vessel and the antigen-antibody reaction is promoted to form the agglutinate of the insoluble carriers.

Upon passage of a prescribed period of time, the reaction solution is sampled from the reaction vessel and dispensed into the sample chamber by the fourth sampling and dispensing means.

The reaction solution dispensed into the sample chamber is transferred to the detecting section, through which the insoluble carriers are passed in the form of a sheathed stream and in which a signal is generated based upon a difference in terms of electrical or optical characteristics. The degree of agglutination of the insoluble carriers is obtained as a numerical value using data indicative of the number of non-agglutinated carriers and the number of agglutinated carriers determined by measuring the signal generated. Converting the value of agglutination makes it possible to quantify the antigen or antibody of interest contained in the specimen.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The drawings illustrate a preferred embodiment of an immunoagglutination measurement apparatus in accordance with the present invention, in which.

DESCRIPTION OF THE PREFERRED EMBODIMENT

A preferred embodiment of an immunoagglutination measurement apparatus according to the invention will now be described with reference to the drawings.

Figure 1:
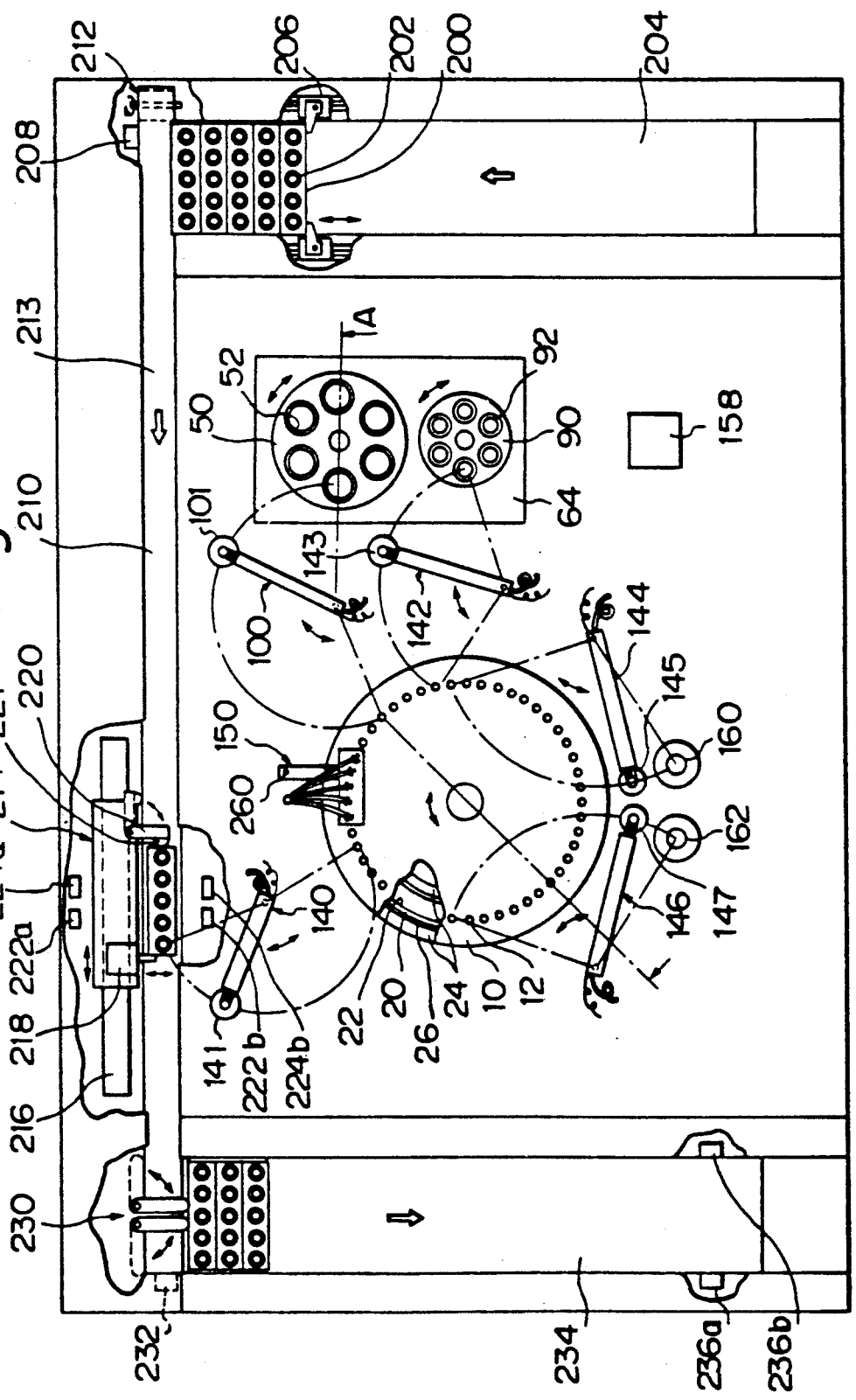
FIG. 1 is a schematic plan view.
Figure 2:
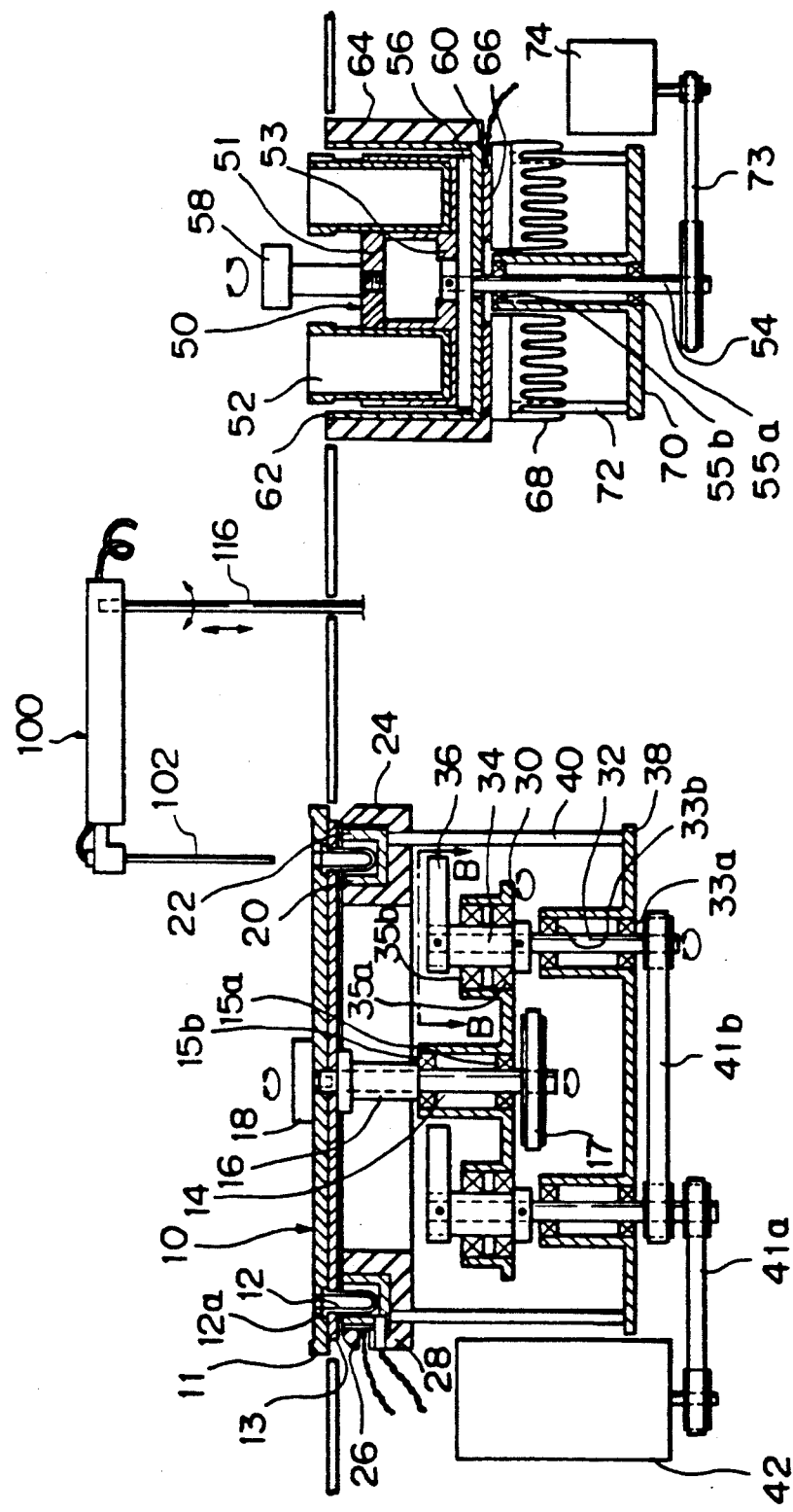
FIG. 2 is a sectional view taken along line A—A of FIG. 1.
Figure 2A:
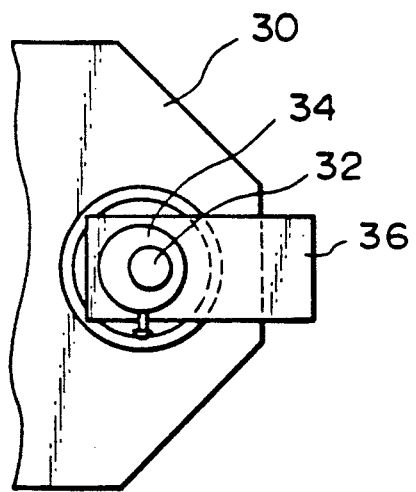
FIG. 2a is a partially enlarged top view as seen from line B—B in FIG. 2.
Figure 3:
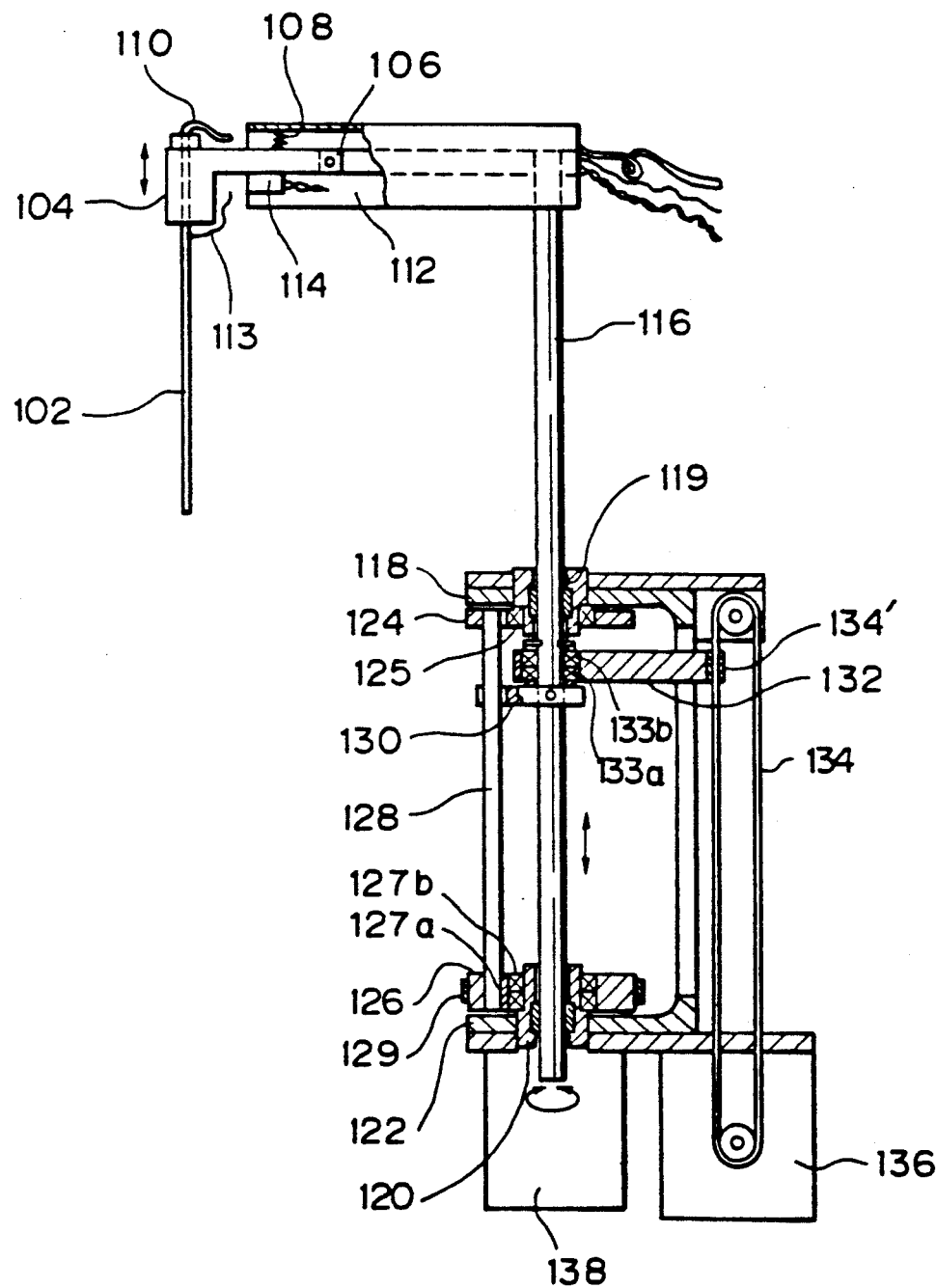
FIG. 3 is a side view of an embodiment of sampling and dispensing means in FIG. 1.
Figure 4:
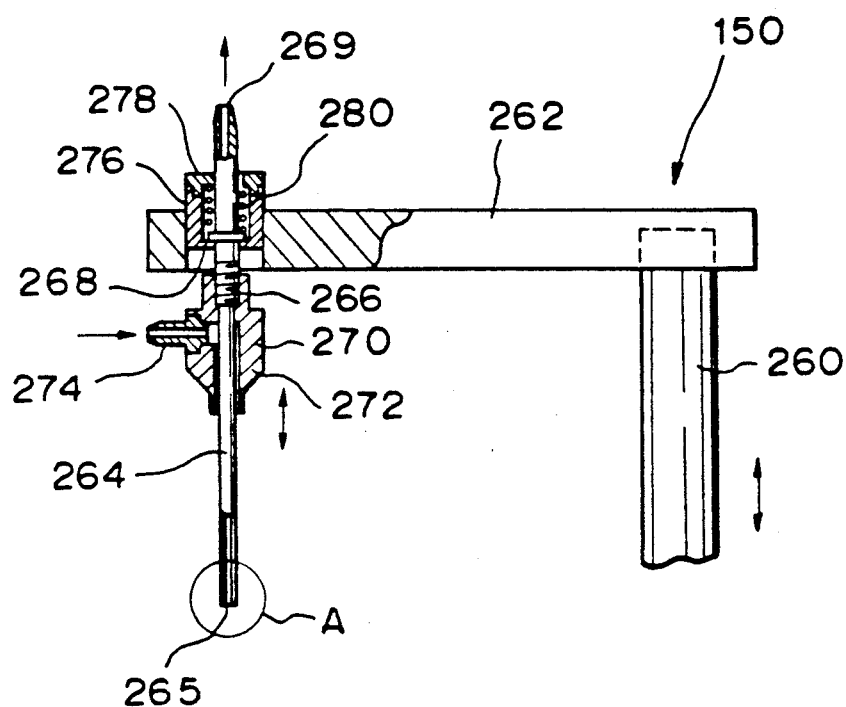
FIG. 4 is a side view of the principal portion of cleansing means shown in FIG. 1.
Figure 4A:
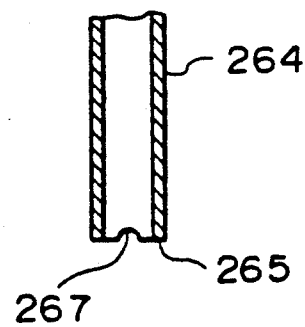
FIG. 4a is an enlarged side view showing a distal end portion of a pipette.

FIG. 1 is a plan view of a preferred embodiment of an immunoagglutination measurement apparatus in accordance with the present invention, FIG. 2 is a sectional view taken along line A—A of FIG. 1, FIG. 2a is a partially enlarged top view as seen from line B—B in FIG. 2, FIG. 3 is a side view of an embodiment of sampling and dispensing means, FIG. 4 is a side view of the principal portion of cleansing means, and FIG. 4a is an enlarged view showing a portion enclosed by a circle A in FIG. 4.

The apparatus shown in FIGS. 1 and 2 includes a disk-shaped reaction table 10 reversibly rotatable together with reaction table shaft 14. The reaction table 10 comprises an upper table 11 and a lower table 13. A total of 48 reaction vessels 12 each of which has a projecting rim 12a are equiangularly supported by the reaction table 10 along its circumference in a state where the projecting rims 12a are clamped between the upper table 11 and lower table 13.

The apparatus also includes a disk-shaped buffer solution table 50 reversibly rotatable together with a shaft 54. The table 50 comprises an upper table 51 and a lower table 53 on which six buffer solution vessels 52 are detachably mounted and equiangularly arranged. The buffer solution is for suppressing a non-specific reaction, which is a cause of measurement error, when specifically measuring the antigen or antibody contained in a specimen, and in this way brings forth the desired specific reaction.

A reversibly rotatable, disk-shaped reagent table 90 is similar to the buffer solution table 50 but slightly smaller in size and detachably mounts six equiangularly arranged reagent vessels 92. The reagent contains insoluble carriers, e.g., latex particles having a diameter of about 0.75 $\mu$m, to the periphery of which are bonded an antibody or antigen that specifically reacts with an antigen or antibody of interest contained in a specimen.

The reaction vessels 12 are maintained at a temperature of, e.g., 43°–47° C., by an isothermal section 20 provided in the lower portion of the reaction table 10. The isothermal section 20, which is made of a material, such as aluminum, having a high thermal conductivity, is provided with a groove 22 surrounding the reaction vessels 12. A sensor 28 for sensing temperature is embedded in the isothermal section 20, a heater 26 whose temperature is controllable is attached to the outer circumference of the isothermal section 20, and the periphery of the isothermal section 20 is covered with a heat insulating material, such as a polyurethane resin, having a low thermal conductivity. The upper table 11 and lower table 13 of the reaction table 10 are also made of a material, such as synthetic resin, exhibiting a low thermal conductivity. As a result, the isothermal section 20 is maintained at a constant temperature irrespective of the ambient temperature and, hence, the temperature of the reaction vessels 12 is held constant.

The rotary reaction table shaft 14 of the reaction table 10 is rotatably supported by a retainer 30 via bearings 15a, 15b and is connected by a belt 17 to a motor (not shown) mounted on the retainer 30. The central portion of the reaction table 10 is attached to the rotary reaction table shaft 14 by a fixture 18 and is supported on the retainer 30 by a support 16. The reaction table 10 is reversibly rotatable relative to the retainer 30 about the reaction table shaft 14. A retainer shaft 34 is freely rotatably supported on the retainer 30 via bearings 35a, 35b and is coupled eccentrically to a shaft 32 freely rotatably supported on a base plate 38 via bearings 33a, 33b. The shaft 32 is connected to a motor 42 by belts 41a, 41b. Accordingly, when the motor 42 rotates, the shafts 32, 34 rotate so that the retainer 30 is shaken relative to the base plate 38, thereby shaking and agitating the reaction table 10.

Attached to the retainer shaft 34 is a static balancer 36 for cancelling vibration, produced by movement of the center of gravity, generated when the reaction table 10 and retainer 30 shake. The static balancer 36 comprises a mass affixed eccentrically to each of the respective retainer shafts 34 to cancel vibration, produced by movement of the center of gravity, when the reaction table 10 and retainer 30 shake.

The buffer solution vessels 52 are kept cool at a temperature of, e.g., 10°-15° C., by an isothermal section 60 provided in the lower portion of the buffer solution table 50. The reagent table 90, which is disposed close to the buffer solution table 50, is of the same construction, hence, the reagent vessels 92 are kept cool in the same manner.

The rotary shaft 54 of the buffer solution table 50 is freely rotatably supported on a base plate 70 via bearings 55a, 55b and is connected to a motor 74 by a belt 73. In order to hold the temperature of the buffer solution vessels constant, the isothermal portion 60, which is made of a material, such as aluminum, having good thermoconductivity, and a radiator 68 are disposed in close contact with a cooling element 66 so as to embrace the same. The cooling element 66 is temperature controllable and utilizes the Peltier effect. The overall arrangement is supported on the base plate 70 by a support 72. The isothermal section 60 is provided with a sensor (not shown) for sensing temperature. A support 56 attached to the shaft 54 is capable of rotating while maintained in good thermal conduction with the isothermal section 60. The buffer solution table 50, which is rotated together with the support 56, is placed on the support 56 in such a manner that the support 56 and lower table 53 come into close thermal contact.

The support 56 and the lower table 53 are both made of a material, such as aluminum, having good thermal conductivity. A cylindrical case 62 provided surrounding the upper table 51 and the buffer solution table 50 is made of a synthetic resin exhibiting little thermal conductivity. The outer circumferences of the case 62 and the isothermal section 60 are covered with a heat insulating material, such as a polyurethane resin, having a low thermal conductivity. Thus, the buffer solution table 50 and the buffer solution vessels 52 are kept cool. A handle 58 is attached to the upper table 51 for the purpose of readily detaching and carrying the buffer solution table 50. This is convenient when changing the buffer solution vessels.

Sampling and dispensing devices 100, 140, 142, 144 and 146 having substantially the same construction will now be described. FIG. 3 is a side view of an embodiment of a sampling and dispensing device 100. The device includes an arm 112 attached at right angles to a shaft 116 rotatably and slidably supported on retainers 118, 122 via guides 119, 120. A pipette 102 is attached to a retainer 104 at the distal end of the arm 112 so as to lie parallel to the shaft 116 when in the normal state. The retainer 104 is rotatably supported on the arm 112 via a shaft 106 under a load applied by a spring 108. The distal end portion of the pipette 102 preferably is formed gradually reduced inner and outer diameters in order to improve sampling and dispensing accuracy. A syringe (not shown) for taking up and discharging liquid is connected to the pipette 102.

A sensor 114 for sensing the retainer 104 is attached to the arm 112. The retainer 104 ordinarily is situated in the vicinity of the sensor 114 under the urging force of the spring 108. However, when the retainer 104 is contacted by a foreign object on descent of the pipette 102, the retainer 104 is rotated about the shaft 106 against the force of the spring 108 and separates from the sensor 114. As a result, an abnormal condition is sensed by the sensor 114. At such time the shaft 116 is immediately raised to elevate the pipette 102. This prevents the pipette from being damaged. Connected to the pipette 102 is a conductor 113 so that a sensor circuit 310, described below, can sense whether the pipette 102 has come into contact with the surface of the liquid in the vessels. Thus, since the liquid level can be sensed even when the height thereof differs, sampling and dispensing can be carried out in a reliable manner.

As evident from FIG. 3, a rotating member 124 rotatably attached to the guide 119 via a bearing 125 and a rotating member 126 rotatably attached to the guide 120 via bearings 127a, 127b are interconnected by a connecting rod 128. The connecting rod 128 has a guide 130 fixedly attached to the shaft 116. The rotating member 126 is connected to a motor 138 by belt 129. Accordingly, when the motor 138 rotates, the rotating member 126 and the connecting rod 128 turn, so that the guide 130 also rotates together with the connecting rod 128. Since the guide 130 is fixedly attached to the shaft 116, the shaft 116 also rotates so that the arm 112 and pipette 102 rotate accordingly.

A coupling member 132 is mounted on the shaft 116 via bearings 133a, 133b attached to the shaft 116 so as to be rotatable about the shaft but whose movement axially of the shaft is limited. A motor 136 is connected to the coupling member 132 by a belt 134 fixed thereto by a belt fixing portion 134'. Accordingly, when the motor 136 rotates, the coupling member 132 is moved up or down. Since the coupling member 132 is attached to the shaft 116 and fixed axially thereof, the shaft 116 also moves up or down. As a result, the arm 112 and the pipette 102 are also movable up or down. Thus, the arm 112 and pipette 102 are capable of reciprocative linear movement axially of the shaft 116 and can rotate reversibly about the shaft 116.

Figure 5:
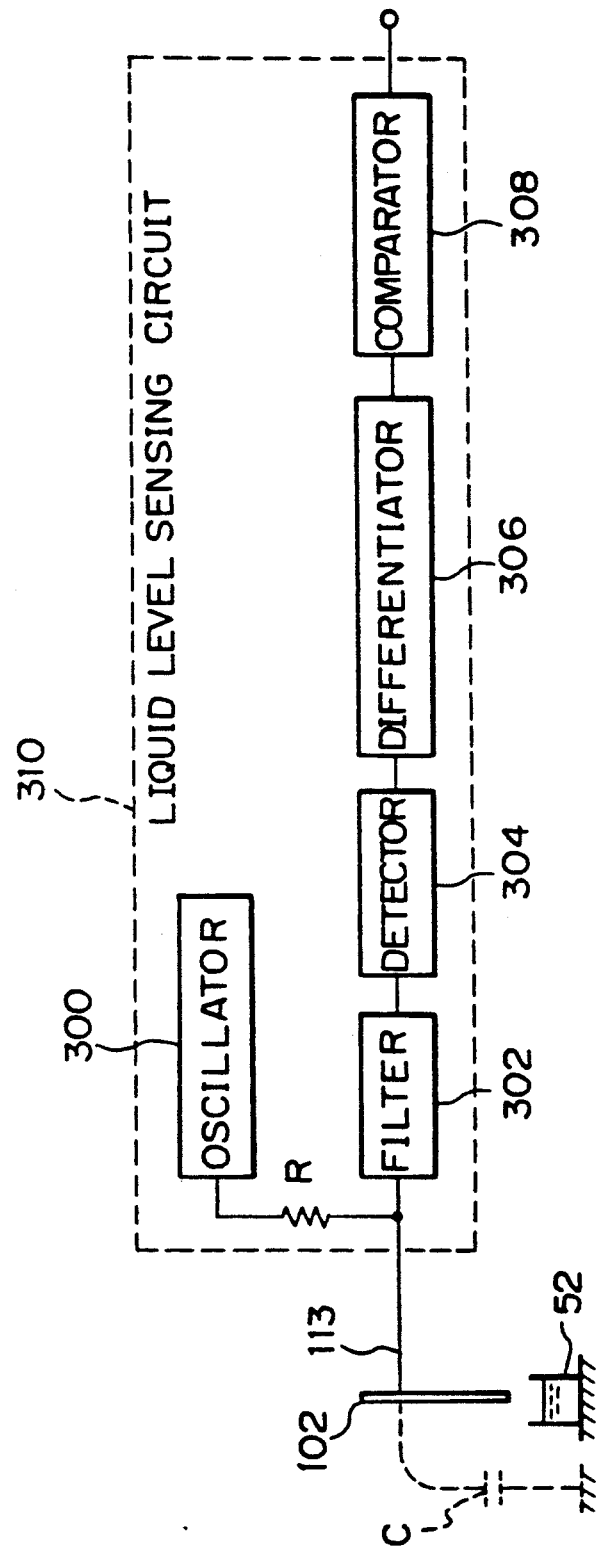
FIG. 5 is a basic structural view of a liquid level detecting circuit.

FIG. 5 is a schematic view of the aforementioned circuit for sensing the liquid level. The conductor 113 connected to the pipette 102 is connected to a high-frequency oscillator 300 having a frequency of, e.g., 2 MHz, via a resistor R having a resistance of, e.g., 10 K-ohms, and to a band-pass filter 302. A detector 304, differentiator 306 and comparator 308 are serially connected to the output side of the filter 302. The buffer solution vessel 52 is placed upon a grounded metal surface. Electric capacitance C between the pipette 102 and the grounded surface varies depending upon whether the tip of the pipette 102 is or is not in contact with the surface of the liquid in the stock solution vessel 52. Accordingly, a high-frequency signal whose amplitude corresponds to the capacitance C is obtained at the output of the RC-type integrating circuit formed by the resistor R and capacitance C, namely at the input to the filter 302. By passing this high-frequency signal through the prescribed band-pass filter 302, the dependence of the amplitude thereof on the capacitance C can be made conspicuous. This high-frequency signal is converted into a DC signal by being detected by the detector 304, and a change in the DC signal level of this DC signal is picked up by the differentiator 306. The output of the differentiator 306 is compared with a predetermined value by the comparator 308, whereby it is sensed whether the pipette 102 has come into contact with the surface of the liquid.

A cleansing device 150 will now be described. FIG. 4 is a side view showing the principal portion of an embodiment of the cleansing device 150. The device includes a shaft 260 reciprocatable linearly by a driving source (not shown). An arm 262 is attached at right angles to the shaft 260. Retainers 276, 278 are attached to the distal end of the arm 262 and receive a pipette 264 that is passed therethrough so as to lie parallel to the shaft 260. A spring 280 embraced by the retainer 278 and a projection on the pipette 264 is provided on the inner side of the retainer 276. Accordingly, when an object strikes the pipette 264 on descent of the shaft 260, the projection 268 compresses the spring 280 so that the pipette 264 can be stopped while in intimate abutting contact with the object. When the shaft 260 rises so that the force acting upon the pipette 264 is removed, the pipette 264 is returned to its lowered state by the action of the spring 280. The upper end of the pipette 264 has a discharge port 269 communicating with a waste liquid recovery section. As shown in FIG. 4a, the lower end of the pipette 264 defines an intake port 265 provided with a notch 267. The latter makes it possible to suck in liquid even when the intake port 265 is in abutting contact with the bottom of the reaction vessel 12. A cleansing part 270 is attached to a threaded portion 266 of the pipette 264 and is provided with a nipple 274, which serves as a supply port, so as to communicate with a gap 272 formed about the periphery of the pipette 264. When a cleaning fluid is supplied by the nipple 274, the solution flows through the gap 272 and is discharged from the periphery of the pipette 264. A plurality of pipettes of the same construction can be mounted on the arm 262 of the cleansing device 150 so that a plurality of adjacent reaction vessels 12 can be washed simultaneously.

The movement of specimen vessels 202 will now be described with reference to FIG. 1. A plurality of racks 200 each have five specimen vessels 202 mounted thereon. Since the racks 200 can be carried individually, this is convenient when loading the specimen vessels. An example of a specimen used is human blood serum.

The racks 200 are set transversely in a dispatch section 204 in a longitudinal array. All of the racks 200 in the dispatch section 204 are moved at one time by a rack moving device 206 in a direction from the bottom to the top of the page in FIG. 1. When the leading rack is sensed by approaching a sensor 208, the moving device 206 stops.

The leading rack is placed upon a belt 213 travelling leftward in FIG. 1 and is thereby moved leftward along a transfer section 210. When the travelling rack 200 contacts a stopper 218 attached to a rack moving device 214, the rack is stopped and an arm 220 having a rubber member 221 attached thereto rotates and urges the rack from behind. The presence of the rack is sensed when the rack approaches sensors 224a, 224b. The rack held between the stopper 218 and the arm 220 is indexed successively by the rack moving device 214 from right to left along a guide 216 by an amount equivalent to one specimen vessel 202. A fixed amount of the specimens is successively taken up from the specimen vessels 202 by the sampling and dispensing means 140 while the presence of the vessels is being confirmed by the sensors 222a, 222b. The rack 200 has five specimen vessel mounting portions each of which is provided with one through-hole, for a total of five through-holes. The presence of the specimen vessels 202 is confirmed when these vessels pass by the sensors 222a, 222b.

When the sampling of the five specimens ends, the stopper 218 and arm 220 return to their original positions to free the rack, after which the rack 200 is moved leftward along the transfer section 210. When the rack 200 is sensed by approaching a sensor 232, the rack is urged into a recovery section 234 by a rack moving device 230. The rack moving device 230 then returns to its original position.

When a rack 200 received by the recovery section 234 is sensed by passing between sensors 236a, 236b, no additional racks 200 can be accommodated by the recovery section 234.

Figure 6:
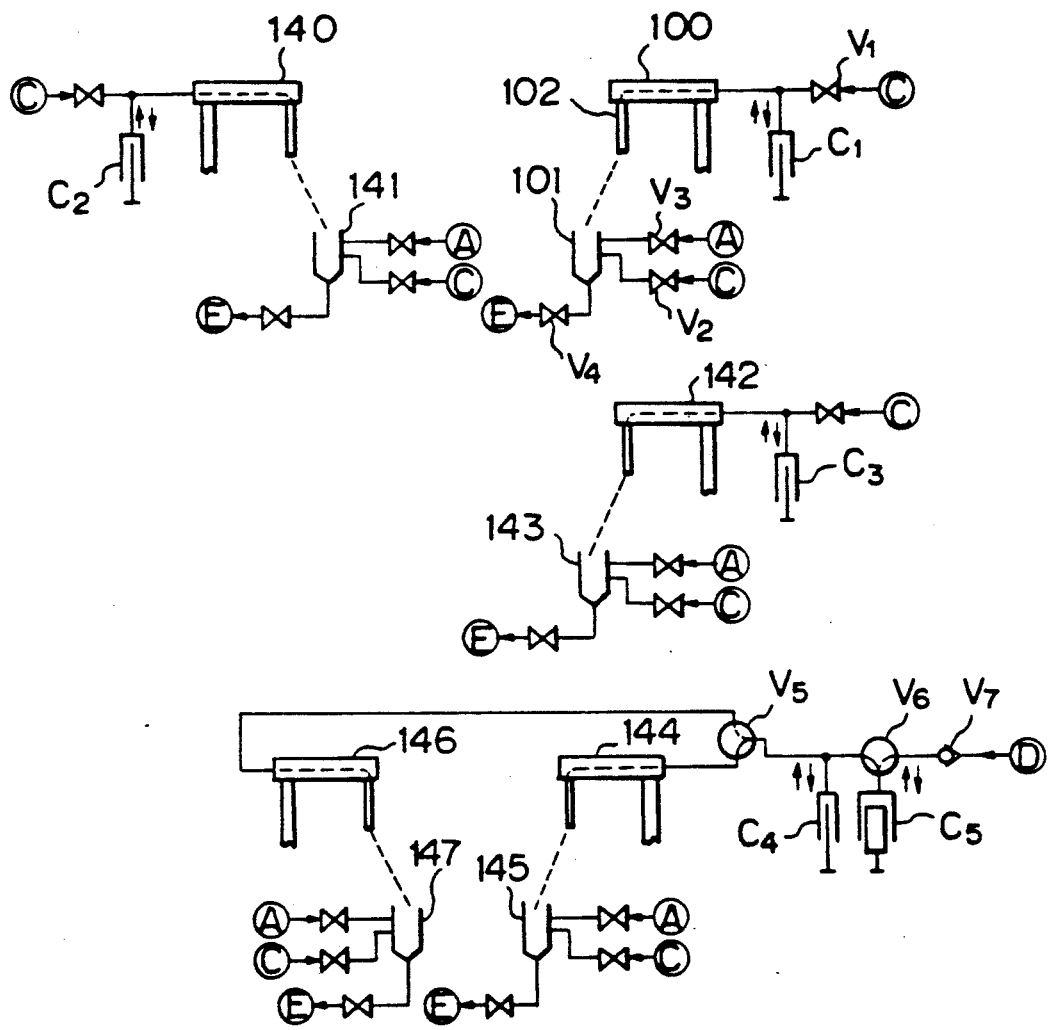
FIG. 6 is a schematic view of hydraulic circuitry peripheral to the sampling and dispensing means.
Figure 7:
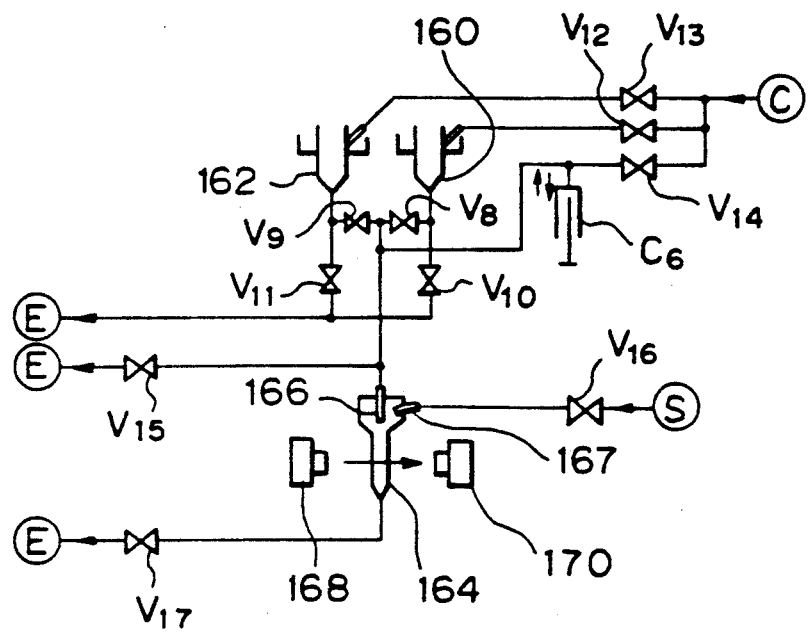
FIG. 7 is a schematic view of hydraulic circuitry peripheral to a detecting section.
Figure 8:
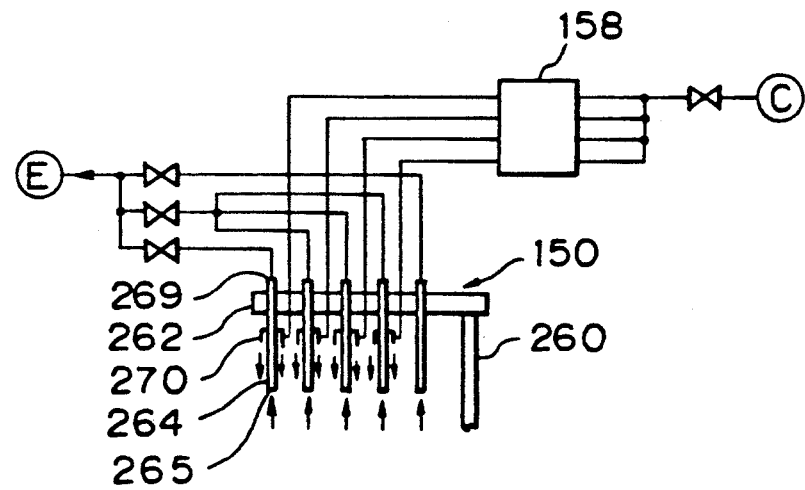
FIG. 8 is a schematic view of hydraulic circuitry peripheral the cleansing means.

The flow of operation of this immunoagglutination measurement apparatus will now be described with reference to FIG. 1 and FIGS. 6 through 8. FIGS. 6 through 8 are schematic views of hydraulic circuitry peripheral to the sampling and dispensing devices 100, 140, 142, 144, 146 (FIG. 6), the detecting section 164 (FIG. 7) and the cleansing device 150 (FIG. 8).

When the sampling and dispensing device 100 operates to bring the pipette 102 into contact with the surface of the buffer solution in a buffer solution vessels at a predetermined position of the buffer solution table 50, the descent of the pipette 102 is halted by detection of the liquid level and a fixed amount, e.g., 80 $\mu$l, of the buffer solution is drawn up from the pipette 102 by lowering a piston of a syringe C1 connected to the pipette. At this time a valve V1 is in the closed state. Next, the sampling and dispensing device 100 is raised, rotated and lowered to dispose the pipette 102 in a reaction vessel at a predetermined position of the reaction table, whereupon the piston of cylinder C1 is raised to dispense the buffer solution taken up earlier. If it is arranged so that the tip of the pipette will contact the surface of the liquid at the end of the dispensing operation, none of the solution will remain attached to the tip. This will improve dispensing accuracy. Thereafter, the sampling and dispensing device 100 is raised, rotated and lowered to dispose the pipette 102 in a cleansing tank 101. The valve V1 is opened, a cleaning fluid is supplied from a cleaning fluid source, and the fluid is discharged from the tip of the pipette 102 to cleanse the inner wall of the pipette. By opening a valve V2, the cleaning fluid is sprayed from the central portion of the cleansing tank 101 so as to strike the outer wall of the pipette 102. As a result, the fluid flows over the outer wall and cleanses the same. The valve V1 is then closed. By opening a valve V3, air is expelled from the upper portion of the cleansing tank so as to impinge upon the pipette 102, thereby blowing off any cleaning fluid clinging to the outer wall and tip of the pipette 102. A valve V4 is opened during cleansing so that the cleaning fluid is recovered in a waste liquid recovery section. If the piston of syringe C1 is lowered further by a very small amount, an air layer can be formed in the tip of the pipette 102. This will make it possible to carry out sampling and dispensing in a state where the buffer solution is isolated from the cleaning fluid.

When the buffer solution has been dispensed into the reaction vessel 12 at the predetermined position by the sampling and dispensing device 100, the reaction table 10 is rotated counter-clockwise by an amount equivalent to nine reaction vessels without waiting for the above-mentioned process for cleansing the sampling and dispensing device 100. A fixed amount, e.g., 10 $\mu$l, of a specimen taken up beforehand by the sampling and dispensing device 140 from a specimen vessel 140 at a predetermined position of the rack is dispensed by the device 140 into the reaction vessel 12 into which the buffer solution has previously been dispensed, thereby mixing the speciment and the buffer solution. The sampling and dispensing operation of the sampling and dispensing device 140 uses a syringe C2 and is similar to that of the sampling and dispensing device 100. Cleansing is also performed in a similar manner using a cleansing tank 141. The reaction table 10 is rotated clockwise by an amount equivalent to ten reaction vessels without waiting for the cleansing of the sampling and dispensing device 140. Thus, buffer solutions and specimens are successively mixed together one after in new reaction vessels efficiently and without waiting time while the reaction table 10 is repeatedly rotated back and forth. By repeatedly rotating the reaction table 10 through nine reaction vessels in the counter-clockwise direction and ten reaction vessels in the clockwise direction, as described above, the net effect is to advance the reaction table 10 clockwise one reaction vessel 12 at a time.

Next, a fixed amount, e.g., 10 $\mu$l, of a reagent is taken up by the sampling and dispensing device 142 from a reagent vessel 92 at a predetermined position of the reagent table 90 and is dispensed by the device 92 into the reaction vessel 12, in which the buffer solution and specimen have been mixed, at a predetermined position, thereby mixing the reagent with the buffer solution and specimen. The sampling and dispensing operation of the sampling and dispensing device 142 uses a syringe C3 and is similar to that of the sampling and dispensing device 100. Cleansing is also performed in a similar manner using a cleansing tank 143. It should be noted that if the reaction table 10 is shaken and agitated at the same time that the specimen and reagent are dispensed into the reaction vessel 12 with the pipettes of the sampling and dispensing devices 140, 142 in contact with or submerged below the surface of the liquid in the reaction vessel 12 when the specimen and reagent are each dispensed, the precision of the dispensing operation is improved and mixing is facilitated.

The reaction vessels 12 are held at a temperature of 43°-47° C., as mentioned earlier. Since the reaction table 10 is shaken and agitated by constant rotation at times other than when it is being rotated clockwise or counter-clockwise, the reaction solution comprising the buffer solution, specimen and reagent in the reaction vessels 12 is agitated uniformly with the passage of time and without variance from one reaction vessel to the next even when the amount of the reaction solution is very small, e.g., 100 $\mu$l. This stabilizes and promotes the latex agglutination reaction caused by the antigen-antibody response. Since a rotor is not used in the reaction vessels, rotor wear is not a problem. This assures stable shaking and agitation over an extended period of time. The larger the rotational diameter and speed of agitation of the reaction table 10, the greater the agitating force obtained. However, too large an agitating force can have the adverse effect of impeding the progress of the latex agglutination reaction. Accordingly, if, by way of example, the inner diameter of the reaction vessel 12 is 8 mm and the amount of reaction solution is 100 $\mu$l, a rotational diameter and speed of agitation of the reaction table 10 of 2-5 mm and 400-1000 rpm, respectively, will be appropriate. Ordinarily, the preferred values are 3 mm and 600 rpm, respectively.

The sampling and dispensing devices 144, 146 are for performing a first measurement (T1 measurement) and a second measurement (T2 measurement), respectively, with regard to a certain reaction solution. The pipettes of these devices are cleansed by respective cleansing tanks 145, 147. Connected to the pipettes of the sampling and dispensing devices 144, 146 are a pipette selection valve V5 for carrying out sampling and dispensing, a syringe C4 for sampling and dispensing the reaction solution, a valve V6 for changing over a diluting solution flow path, a check valve V7 and a diluting solution dispensing syringe C5. When the valve V6 is switched over to a diluting solution supply source and the piston of syringe C5 is lowered, a fixed amount of the diluting solution is taken up in the syringe C5. When the valve V6 is switched over to the pipette side and the piston of the syringe C5 is raised, a fixed amount of the diluting solution is dispensed from either of the pipettes. When the valve V5 is switched over to either of the pipettes and the piston of syringe C4 is lowered or raised, the reaction solution can be sampled by or dispensed from the selected pipette. If the diluting solution is also dispensed at the same time as the reaction solution, the reaction solution will be diluted. The valve V7 acts to mitigate pressure shock produced when the valve V6 is changed over.

With the sampling and dispensing device 144 switched over, a fixed amount, e.g., 30 $\mu$l, of the reaction solution is taken up by the device 144 from a reaction vessel 12 at a predetermined position of the reaction table 10, and a prescribed time, e.g., 24 seconds, after mixing the reaction solution is dispensed into the sample chamber 160 together with 1 ml of the diluting solution. It should be noted that since only 0.5 ml of the diluting solution will have been previously dispensed into the sample chamber 160 by the syringe C5, the 30 $\mu$l of reaction solution will be embraced by 0.5 ml and 1 ml of diluting solution and therefore will be effectively diluted by 51 times within the sample chamber 160. As seen from the specimen, this represents dilution by 510 times. The resulting diluted sample is for the T1 measurement.

As for the remaining 70 $\mu$l of reaction solution, the valve V5 is switched over and a prescribed time, e.g., 14 minutes and 36 seconds, after mixing, the reaction solution is dispensed into the sample chamber 162 together with the diluting solution to dilute the reaction solution by 51 times. Thus is prepared a dilute sample of the reaction solution for the T2 measurement. It should be noted that dilution can be performed by using a sheathing solution rather than a diluting solution.

FIG. 7 is a schematic view of hydraulic circuitry peripheral to a flowcell 164 serving as a detector for detecting the latex agglutinate. Opening valves V8, V15 fills a flow passage with 1530 $\mu$l of the diluted sample for T1 measurement prepared in the sample chamber 160 by the sampling and dispensing device 144. The valves V8, V15 are subsequently closed, followed by opening a valve V17. Raising the piston of syringe C6 at a prescribed speed causes the diluted sample to be expelled from a nozzle 166 at a fixed flow velocity. When a valve V16 is opened at this time, a sheathing solution is supplied at a fixed pressure from a supply port 167 at the upper side surface of the flowcell. The diluted sample flows through the center of the flowcell 164 in the form of a fine stream enveloped by the sheathing solution. The stream of the sample is irradiated with light in the form of a spot and light scattered from individual particles is optically detected.

Figure 9:
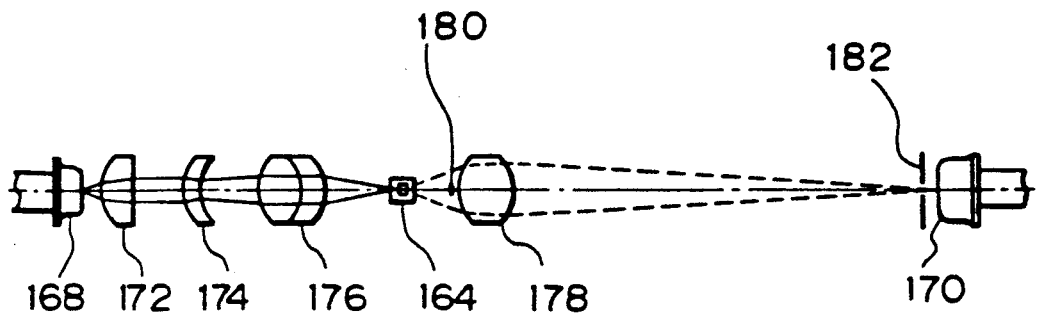
FIG. 9 is a plan view of an optical detecting section.

FIG. 9 is a plan view of the optical detecting device. Laser light generated by a light-emitting element 168 and having a wavelength of, e.g., 780 nm, is condensed by lenses 172, 174, 176 to form a spot of light on the central portion of the flowcell 164. Transmission of the scattered light from the flowcell is blocked by a light-shielding plate 180 and only forward-scattered light is condensed by a lens 178 to irradiate a light-receiving element 170, whereby the light is converted into an electric signal. Stray light is blocked by a light-shielding plate 182 to improve the forward-scattered light detection sensitivity.

During the detection of the particles within the flowcell 164, the syringe C6 expels the diluted sample from the nozzle 166. Since the valves V16, V17 are open and the valve V8 is closed while this is being carried out, the sample chamber 160 is cleansed while making effective use of time. The diluted sample remaining in the sample chamber 160 is discharged by opening a valve V10. A cleaning fluid, which is supplied from the upper portion of the sample chamber 160 by opening a valve V12, cleanses the inner wall of the chamber before being discharged. The cleaning fluid is supplied again, some of the fluid passing through the valve V10 to cleanse the same before being discharged. When the syringe C6 has expelled a predetermined amount of the diluted sample, operation of the syringe C6 is halted and only the sheathing solution is supplied from the supply port 167 and passes through the valve V17 to be discharged. As a result, the interior of the flowcell 164 is cleansed, after which the valves V16, V17 are closed. Opening the valves V8, V15 discharges the cleaning fluid from the sample chamber 160 so that the fluid may flow through and cleanse the flow passageway previously filled with the sample for measurement. Next, the valve V8 is closed and the valve V10 is opened to completely discharge the cleaning fluid from within the sample chamber 160. Valve V14 is also opened to permit further cleaning. Next, the valves V15, V16 are opened to supply the sheathing solution to the supply port 167, the solution being discharged by flowing backwardly through the nozzle 166. The nozzle 166 is thus cleansed. In FIG. 7, it is possible to perform cleansing by using the sheathing solution instead of the cleaning fluid.

The diluted sample for the T2 measurement is prepared in the sample chamber 162 by the sampling and dispensing device 146 in a manner similar to that described above. Valves V9, V11 function instead of the valves V8, V10 to carry out measurement and cleansing in a manner similar to the foregoing.

Figure 10:
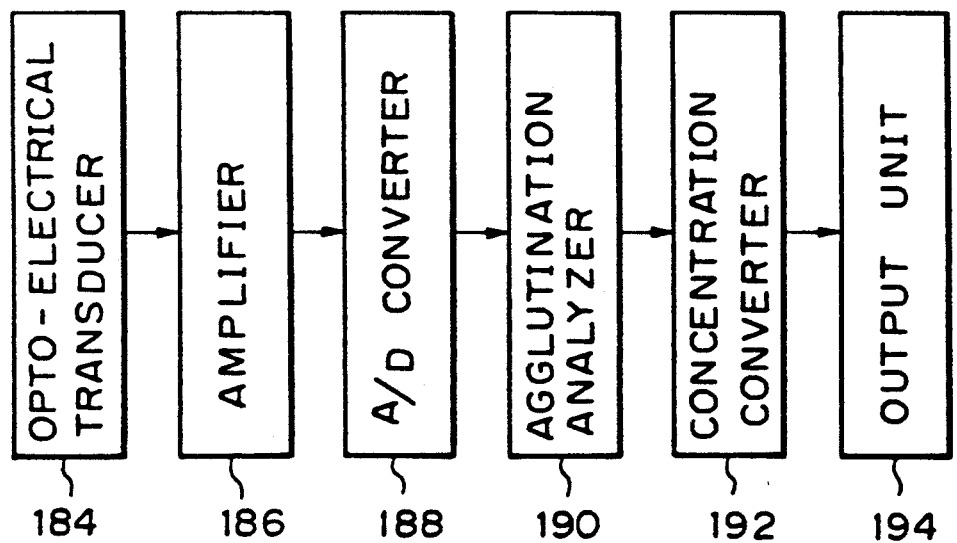
FIG. 10 is a basic structure view of a measurement circuit.
Figure 11:
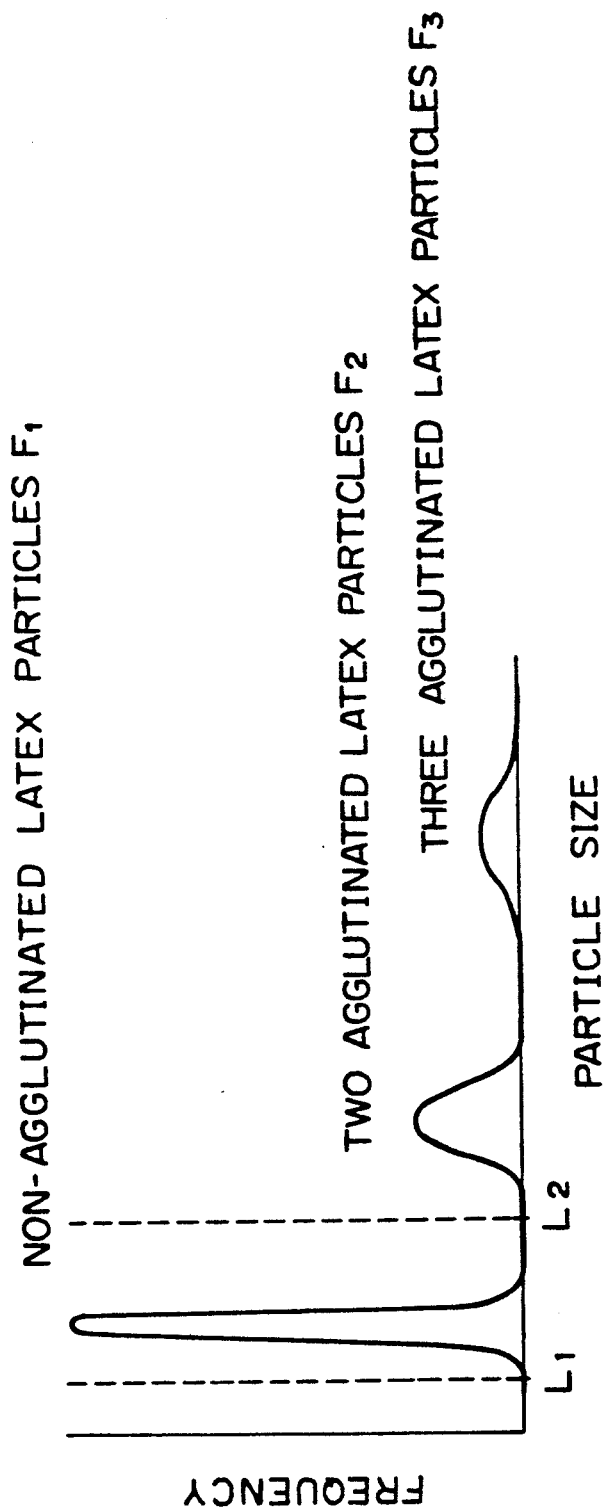
FIG. 11 is a distribution of particle sizes conforming to the degree of agglutination.

FIG. 10 is a schematic view of a measurement circuit which includes an opto-electrical transducer 184. The transducer 184, which has a light-receiving element 170 and is capable of a high-speed response, is described in, e.g., the specification of Japanese Utility Model Application No. 62-197153. The transducer 184 produces an electric signal the magnitude whereof corresponds to the size of detected particles. Using such a high-speed opto-electrical transducer makes it possible shorten measurement time by allowing the particles to be passed through the flowcell 164 faster than in the prior art. The output signal of the transducer 184 representing detected particles is amplified by an amplifier 186, and the amplified signal is subjected to an A/D conversion by an A/D converter 188. As a result, crest values indicative of individual particles are obtained in the form of digital values. This digital data is stored in memory and the particles represented thereby are counted. This is followed by displaying a distribution of the particle sizes, as shown in FIG. 11. The output of the A/D converter 188 is applied to analyzing means 190, in which there are set, by way of example, a level L1 for distinguishing between noise and non-agglutinated latex particles F1, and a level L2 for distinguishing between non-agglutinated particles F1 and two agglutinated latex particles F2. By setting these levels, it is possible to calculate the number of particles whose sizes are greater than the level L1 (which number is the sum of the number M of non-agglutinated latex particles and the number P of agglutinated latex particles) and the number of particles whose sizes are greater than the level L2 (the number P of agglutinated latex particles). Agglutination degree Y can then be obtained as a numerical value using the formula $Y=P/(M+P)$. In order to obtain the agglutination degree Y as a numerical value, Y can be defined by another method which does not rely upon this formula, and Y can then be converted into a numerical value in accordance with this definition. Methods of accomplishing this are described in the specifications of, e.g., Japanese Patent Application Laid-Open Nos. 60-111963 and 60-243565. The agglutination degree Y obtained by the analyzing means 190 is converted into concentration by concentration converting means 192, the output of which is delivered to an output unit 194.

Figure 12:
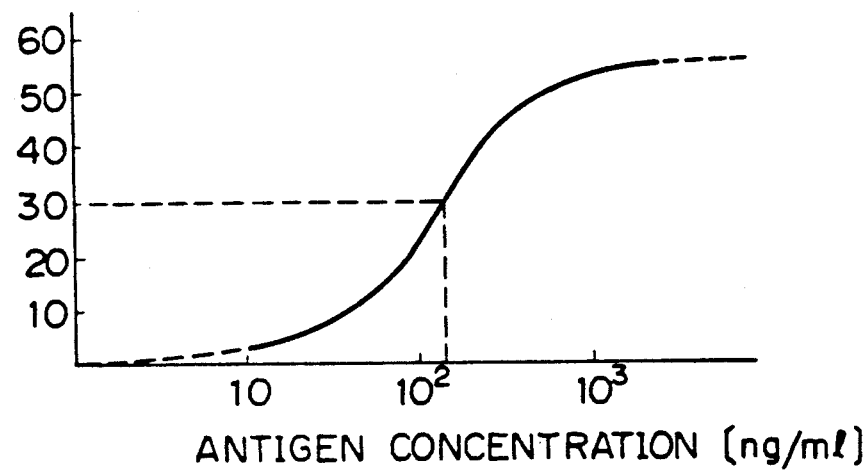
FIG. 12 shows a calibration curve.
Figure 13:
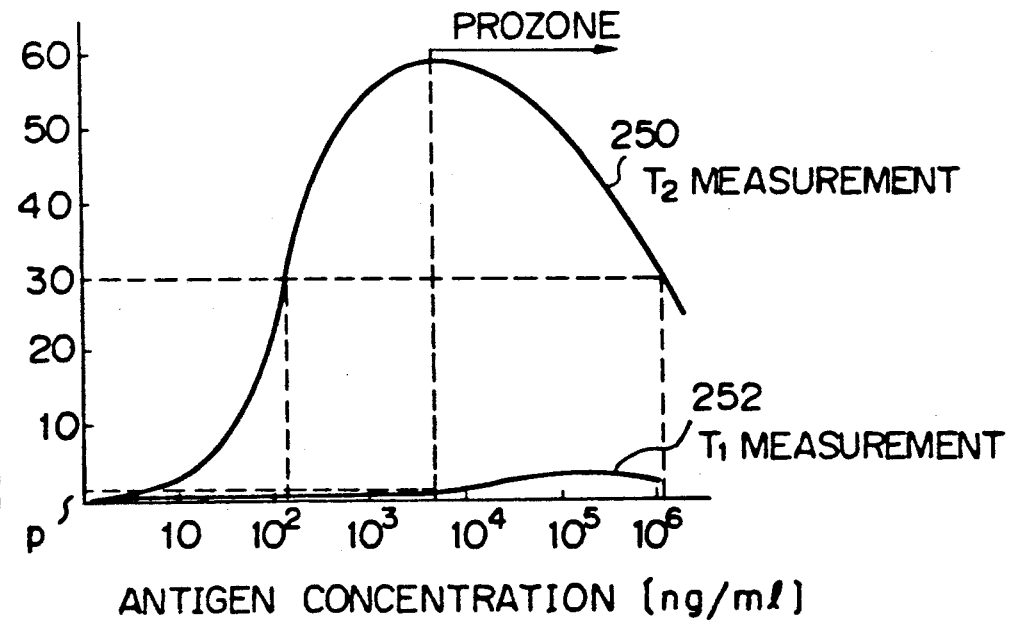
FIG. 13 shows antigen concentration-agglutination curves.

FIG. 12 is an example of a calibration curve showing the relation between concentration and the agglutination degree Y at such time using a known concentration calibrator. Concentration can be found from the degree of agglutination by applying the value of Y obtained in the T2 measurement to the calibration curve of FIG. 12. However, in a so-called excessive region (prozone) in which the concentration of a prescribed antigen contained in a specimen is too high, there is a tendency for the latex agglutination reaction to be suppressed. FIG. 13 shows concentration-agglutination curves illustrating this suppression phenomenon, in which numerals 250, 252 denote concentration-agglutination curves at T2 measurement and T1 measurement, respectively. As indicated by the concentration-agglutination curve 250 for T2 measurement, the degree of agglutination rises when the antigen concentration increases in the low-concentration region, whereas the degree of agglutination becomes smaller the higher the antigen concentration becomes in the prozone. Accordingly, the antigen concentration cannot be uniquely determined from the value of the degree of agglutination. This means that it is necessary to confirm, for each and every specimen, that the degree of agglutination obtained in the T2 measurement is not a degree of agglutination obtained in the prozone. To this end, for example, it is useful to consider a case in which T1 measurement is carried out at a suitable time prior to T2 measurement and the value of the degree of agglutination thus obtained rises when the antigen concentration rises. In other words, the value of the degree of agglutination (curve 252) in the T1 measurement is compared with the degree of agglutination p in the T1 measurement corresponding to the lower limit concentration of the prozone, in which p serves as a criterion. If p is exceeded, this means that the degree of agglutination is in the prozone.

Thus, the sample prepared by the sampling and dispensing device 144 is used in a first measurement (T1 measurement), the sample prepared by the sampling and dispensing device 146 is used in a second measurement (T2 measurement), and it is judged whether the degree of agglutination is inside or outside the prozone.

The reaction vessel 12 containing unnecessary reaction solution at the end of a measurement arrives at the cleansing device 150, which has five pipettes. FIG. 8 is a schematic view of hydraulic circuitry peripheral to the cleansing device 150. When a shaft 260 is lowered, the five pipettes descend simultaneously and can be brought into contact with the bottom of the reaction vessel 12. The reaction solution is drawn up by each pipette from the intake port 265 provided with the notch 267 and is discharged into a waste recovery section from the discharge port 269. The cleaning fluid is supplied to the cleansing section 270 from a pump 158 and is discharged from the outer periphery of each pipette, thereby cleansing the outer walls of the pipettes and the inner walls of the reaction vessels. The cleaning fluid is again drawn up and discharged by the pipettes. By repeating this, two cleansing operations are performed per pipette. The shaft 260 and the five pipettes 264 are then raised and the reaction table 10 is rotated. The same cleansing operation is carried out each time the reaction vessels 12 are indexed by one vessel in the clockwise direction. Thus, each single reaction vessel is successively cleansed by four pipettes, for a total of eight cleansing operations, as a result of which all of the reaction solution is completely removed from the reaction vessel. Since the fifth pipette is not provided with the cleansing section 270, this pipette merely performs a sucking operation and is not supplied with the cleaning fluid. The end result is that all of the liquid in the reaction vessel 12 is eventually removed. In accordance with the present invention, a rotor used in the prior art is not employed in the reaction vessel 12. This facilitates cleansing of the reaction vessel and solves the problem of cleaning fluid left attached to the rotor. As a result, there is no adverse effect upon the measurement of the next specimen. In addition, it is possible to perform a variety of highly precise measurements relating to the antigen-antibody reaction by virtue of the reaction promoting effect and long-term stability of the reaction state brought about by the aforementioned shaking and agitating motion.

Furthermore, in accordance with the invention, the quantity of one substance in a specimen can be measured by a single measurement. However, since the buffer solution table 50 and reagent table 90 can each have a plurality of vessels mounted thereon, a plurality of buffer solution vessels 52 and a plurality of reagent vessels 92 can be provided in accordance with the types of substances to be measured, and items for measurement can be preset. If this is done, measurement results for a plurality of substances or a number of items can be obtained at all times. Examples of antigen capable of being measured include α-fetprotein (AFP), carcinoembryonic antigen (CEA), ferritin (FRN) and $\beta_2$-microglobulin ($\beta_2$-m). It has been clarified that linearity of measurement is maintained in the concentration ranges of 2–1,000 ng/ml for AFP, 1–250 ng/ml for CEA, 2–1,000 ng/ml for FRN and 255–10,200 ng/ml for $\beta_2$-m.

Whereas the sampling and dispensing device in the prior art is for multi-purpose use, namely for the buffer solution, specimen T1 measurement and T2 measurement, the sampling and dispensing devices in the apparatus of the present invention are completely independent of one another. Since this makes it possible to eliminate the waiting time which arises in the prior art as at the time of cleansing, the various operations performed by the sampling and dispensing devices can be carried out while overlapping one another in terms of time. As a result, specimen processing capability per unit time is greatly improved, as evidenced by the fact that the immunoagglutination measurement apparatus is capable of processing as many as 150 specimens per hour.

As described above, the immunoagglutination measurement apparatus of the invention has the following outstanding advantages:

(a) Since stirring to promote and stabilize the antigen-antibody reaction is performed by agitation produced by shaking, a stable agglutination reaction is promoted even with half the amount of reaction solution used in the prior art, and agitation is performed uniformly without variance from one reaction vessel to another. This makes it possible to reduce the required amount of buffer solution, specimen and reagent each by half.

(b) Since a rotor is not used to stir the reaction solution, there is no longer any risk of rotor or vessel wear, uniform stirring of the entire contents of the reaction vessel can be assured and it is possible to achieve accurate measurement and excellent reproducibility. In addition, the reaction vessels can be completely cleansed and stable measurement results can be obtained with greater sensitivity.

(c) Since the sampling and dispensing devices for the buffer solution, specimen, reagent and reaction solution are used exclusively for these materials and operate independently of one another, the various sampling and dispensing operations can be executed very efficiently with little waiting time. The result is a major improvement in specimen processing capability.

(d) Measurement can be performed in a successive manner merely by mounting the specimen vessels on racks and arranging the racks in side-by-side fashion in the dispatch section. This facilitates the handling of the specimen vessels.

As many apparently widely different embodiments of the present invention can be made without departing from the spirit and scope thereof, it is to be understood that the invention is not limited to the specific embodiments thereof except as defined in the appended claims.

What is claimed is:

1. An immunoagglutination measurement apparatus for mixing together a specimen from a specimen vessel and a reagent, said apparatus comprising:
   a base;
   a reversibly rotatable buffer solution table mounted on said base and on which a plurality of buffer solution vessels are mounted;
   a first temperature regulating means in thermal communication with the buffer solution vessels for maintaining the buffer solution vessels in an isothermal state;
   a reversibly rotatable reagent table mounted on said base and on which a plurality of reagent vessels are mounted;

a second temperature regulating means in thermal communication with the reagent vessels for maintaining the reagent vessels in an isothermal state;

a reversibly rotatable and shakable reaction table mounted on said base and on which a plurality of reaction vessels are supported;

a third temperature regulating means in thermal communication with the reaction vessels for maintaining the reaction vessels in an isothermal state;

first sampling and dispensing means mounted to said base for sampling a buffer solution from the buffer solution vessels and dispensing the buffer solution into the reaction vessels;

second sampling and dispensing means mounted to said base for sampling a specimen from the specimen vessels and dispensing the specimen into the reaction vessels;

third sampling and dispensing means mounted to said base for sampling a reagent from the reagent vessels and dispensing the reagent into the reaction vessels;

fourth sampling an dispensing means mounted to said base for sampling a reaction solution, in which an agglutination reaction is brought about by mixing of the buffer solution, specimen and reagent, from the reaction vessels and dispensing the reaction solution into a sample chamber communicating with a detection section;

a retainer;

a reaction table shaft integrally attached to said reaction table, said reaction table shaft having a proximal end freely rotatably attached to said retainer and a distal end integrally attached to said reaction table to freely rotatably support said reaction table for rotation about a central axis defined by said reaction table shaft;

one or more retainer shafts freely rotatably attached to said base at a proximal end of the retainer shafts, and eccentrically coupled to said retainer at a distal end thereof whereby rotation of the retainer shafts effects shaking of the retainer relative to the base, thereby shaking the reaction table;

a static balancer attached to said one or more retainer shafts for rotation therewith to reduce vibrations produced by movement of the center of gravity of the retainer and reaction table; and measurement means for measuring the amount of agglutinization of the reaction solution.

2. The apparatus according to claim 1, further comprising:

a first driving source connected to said reaction table shaft to rotate the reaction table shaft and rotate the reaction table integral therewith about said central axis;

a second driving source coupled to said one or more retainer shafts to produce said vibrations of the retainer and the reaction table connected thereto;

an isothermal section provided with an annular groove in which the reaction vessels reside so as to be surrounded by the isothermal groove and having temperature-controllable elements attached thereto in close proximity to one another;

a thermal insulating material provided so as to cover a periphery of said isothermal section; and said reaction table being reversibly rotatable and shakable while the reaction vessels are maintained in an isothermal state.

3. The apparatus according to any one of claims 1 or 2, wherein said apparatus further includes cleansing means for cleaning vessels utilized with said apparatus, said cleansing means comprising:

a reciprocatable shaft linearly reciprocatable in the axial direction defined by said shaft;

a connecting arm having a proximal end integral with said reciprocatable shaft and a distal end;

a pipette supportingly engaged by said supporting arm at said distal end thereof, and extending in said axial direction, said pipette having an intake port and a discharge port;

a recovery station in fluid communication with said discharge port for receiving fluid discharged from said discharge port, said recovery station including aspirating means for withdrawing liquid from said discharge port and storage means for storing said withdrawn liquid;

a cleansing retainer attached to said pipette intermediate of said intake end and said discharge end and extending about the periphery of a portion of said pipette, said retainer defining a discharge gap between said cleansing retainer and the periphery of said pipette;

a cleansing fluid inlet duct integral with said cleansing retainer and in fluid communication with said cleansing fluid inlet duct, with cleansing fluid entering said inlet duct being discharged through said discharge gap and onto the periphery of said pipette; and shaft reciprocating means for axially reciprocating said shaft between a first position in which said inlet port of said pipette is adjacent the bottom of said vessel and a second position in which said inlet port is spaced from the vessel.

* * * * *

UNITED STATES PATENT AND TRADEMARK OFFICE
CERTIFICATE OF CORRECTION

PATENT NO. : 5,215,714
DATED : June 1, 1993
INVENTOR(S) : Satoru OKADA, et al.

It is certified that error appears in the above-identified patent and that said Letters Patent is hereby corrected as shown below:

ON THE TITLE PAGE:

On the Title Page under the heading "[73] Assignee:" change "Kobe" to read --Hyogo-ken--.

On the Title Page under the heading "[56] References Cited - U.S. PATENT DOCUMENTS" change "Scordata" to read --Scordato--.

In Column 9, line 15, change "speciment" to read --specimen--.

Signed and Sealed this

Fifteenth Day of March, 1994

Attest:

BRUCE LEHMAN

*Attesting Officer*     *Commissioner of Patents and Trademarks*